(12) United States Patent
Wang et al.

(10) Patent No.: US 10,052,378 B2
(45) Date of Patent: Aug. 21, 2018

(54) PHARMACEUTICAL COMPOSITIONS COMPRISING CPG OLIGONUCLEOTIDES

(71) Applicant: Changchun Huapu Biotechnology Co., LTD., Changchun, Jilin Province (CN)

(72) Inventors: Ligong Wang, Beijing (CN); Yan Shao, Beijing (CN)

(73) Assignee: Changchun Huapu Biotechnology Co., LTD., Changchun (CN)

( * ) Notice: Subject to any disclaimer, the term of this patent is extended or adjusted under 35 U.S.C. 154(b) by 0 days.

(21) Appl. No.: 15/319,351

(22) PCT Filed: Jun. 12, 2015

(86) PCT No.: PCT/CN2015/081330
§ 371 (c)(1),
(2) Date: Dec. 15, 2016

(87) PCT Pub. No.: WO2015/196935
PCT Pub. Date: Dec. 30, 2015

(65) Prior Publication Data
US 2017/0136119 A1    May 18, 2017

(30) Foreign Application Priority Data

Jun. 26, 2014  (CN) .......................... 2014 1 0294142

(51) Int. Cl.
*A61K 39/00* (2006.01)
*A61K 39/39* (2006.01)
*A61K 39/095* (2006.01)
*A61K 39/02* (2006.01)
*A61K 39/385* (2006.01)
*A61K 39/29* (2006.01)
*C12N 7/00* (2006.01)

(52) U.S. Cl.
CPC ............ *A61K 39/292* (2013.01); *A61K 39/39* (2013.01); *C12N 7/00* (2013.01); *A61K 2039/54* (2013.01); *A61K 2039/545* (2013.01); *A61K 2039/55505* (2013.01); *A61K 2039/55561* (2013.01); *C12N 2730/10134* (2013.01)

(58) Field of Classification Search
CPC ........ A61K 39/12; A61K 39/08; A61K 39/05; A61K 2039/70; C12N 2730/10134
See application file for complete search history.

(56) References Cited

PUBLICATIONS

Zhang et al., Enhanced specific immune responses by CpG DNA in mice immunized with recombinant hepatitis B surface antigen and HB vaccine, 2011, Virology Journal, 8:1-6.*
Zhang et al. Enhanced specific immune responses by CpG DNA in mice immunized with recombinant hepatitis B surface antigen and HB vaccine, Virology Journal, 2011, 8(78):1-6.*
HogenEsch, "Mechanism of immunopotentiation and safety of aluminum adjuvants", 2013, frontiers in immunology, 3:1-13.*
Xiao Min Mu et al., Journal of Tropical Medicine, pp. 833-835, 2007.
English translation of abstract for Xiaomin et al., Journal of Tropical Medicine, 2007.
Zhang et al., Enhanced specific immune responses by CpG DNA in mice immunized with recombinant hepatitis B surface antigen and HB vaccine, Virology Journal, 2011, 8:78.

* cited by examiner

*Primary Examiner* — Barry A Chestnut
(74) *Attorney, Agent, or Firm* — K&L Gates LLP; Louis C. Cullman; David Diamond

(57) ABSTRACT

The present invention provides a pharmaceutical composition for inducing immune response in a subject, comprising: (a) an antigen with a concentration ranging from 1 μg/ml to 100 μg/ml; (b) CpG oligonucleotides having a sequence of 5'-tcgacgttcgtcgttcgtcgttc-3', with a concentration ranging from 25 μg/ml to 500 μg/ml, and (c) an aluminum adjuvant with a concentration ranging from 25 μg/ml to 500 μg/ml. Such pharmaceutical composition can induce or boost immune response against antigen in the subject.

8 Claims, 5 Drawing Sheets

PHARMACEUTICAL COMPOSITIONS COMPRISING CPG OLIGONUCLEOTIDES

CROSS REFERENCE TO RELATED APPLICATIONS

This application claims the benefit of, and priority to, Chinese Patent Application Serial No. 201410294142.3, filed on Jun. 26, 2014, the entire disclosures of which are hereby incorporated by reference in their entireties.

FIELD OF THE INVENTION

Generally, the present invention relates to a pharmaceutical composition comprising CpG oligonucleotides. In particular, the present invention relates to a pharmaceutical composition for boosting immune response against an antigen, depending on synergistic effect of CpG oligonucleotides and aluminium adjuvants.

BACKGROUND OF THE INVENTION

Hepatitis B virus (HBV) leads to public health issues and thus attracts global concern. Utilization of vaccines is able to effectively prevent infection of HBV, reduces chronic hepatitis carrier rate and controls prevalence of HBV. According to the report from WTO, 1 billion doses of Hepatitis B virus vaccines have been used worldwide since 1982, which play a critical role in preventing and controlling the spread of hepatitis B virus. As replication of HBV follows RNA-based replication that is error-prone, HBV-resistant escape mutants in which hepatitis B surface antigens (HBsAg) are altered occur. So far, commercial Hepatitis B vaccines for the purpose of prevention contain aluminium hydroxide (Al(OH)$_3$) as an adjuvant. Such adjuvant is able to enhance Th2 type immune response and humoral immunity, and can induce production and secretion of protective antibody IgG1. Aluminium hydroxide functions on storing antigens and delaying clear of antigens, and thus the antigens can be exposed to immune system for an extended time period. Meanwhile, aluminium hydroxide also functions on activating complements, enhancing decoy capacity of lymph node and extending residence time of lymph cells. Further, aluminium hydroxide is able to adsorb antigens and transport them to lymph node, thereby producing immune response. Aluminium hydroxide is also able to coat and gradually release antigens, thereby playing a role of reservoir of antigens. However, with the development of vaccinology and immunology, aluminium hydroxide as an adjuvant has some limitations. For example, aluminium hydroxide mainly stimulates production of Th2-related antibodies (including IgE), but it neither induces Th1 cell immune response to stimulate activity of Th1, nor enhances cellular immunity (CTL) to block activation of CD8+CTL. Although Th2-related antibodies are able to neutralize virus outside cells, it cannot completely clean hepatitis B virus hiding in the infected cells, thereby usually resulting in hiding of hepatitis B virus in patients. Moreover, about 10% of population has low response or no response to the commercial vaccines as mentioned above. Therefore, it is of importance to enhance immune activity of current Hepatitis B virus vaccine and develop a vaccine that can effectively clean hepatitis B virus hiding in cells.

SUMMARY OF THE INVENTION

In one aspect, the present invention provides a pharmaceutical composition for inducing immune response in a subject, comprising (a) an antigen with a concentration ranging from 1 μg/ml to 100 μg/ml, (b) CpG oligonucleotides having a sequence of 5'-tcgacgttcgtcgttcgtcgttc-3', with a concentration ranging from 25 μg/ml to 500 μg/ml, and (c) an aluminium adjuvant with a concentration ranging from 25 μg/ml to 500 μg/ml.

In one embodiment of the present invention, the sequence of the said CpG oligonucleotides is 5'-tcgacgttcgtcgtcgtcgttc-3', the said aluminium adjuvant is aluminium hydroxide, the antigen is a virus-related antigen. Preferably, the virus is selected from hepatitis virus, such as recombinant human hepatitis B virus. The antigen is hepatitis B surface antigen.

In the pharmaceutical composition of the present invention, the aluminium adjuvant has a concentration ranging from 25 μg/ml to 125 μg/ml, or from 125 μg/ml to 500 μg/ml, or from 125 μg/ml to 400 μg/ml, or from 125 μg/ml to 300 μg/ml, or from 250 μg/ml to 500 μg/ml, or from 300 μg/ml to 400 μg/ml, or from 400 μg/ml to 500 μg/ml, or from 300 μg/ml to 500 μg/ml. The said CpG oligonucleotides (CpG-ODN) with a sequence of 5'-tcgacgttcgtcgttcgtcgttc-3' have a concentration ranging from 125 μg/ml to 500 μg/ml, or from 25 μg/ml to 125 μg/ml, or from 125 μg/ml to 250 μg/ml, or from 250 μg/ml to 500 μg/ml. The antigen has a concentration of 20 μg/ml.

According to the preferable embodiment of the present invention, in the pharmaceutical composition of the present invention, the antigen has a concentration of 20 μg/ml, the aluminium adjuvant has a concentration ranging from 250 μg/ml to 500 μg/ml, or from 300 μg/ml to 500 μg/ml, and the CpG-ODN has a concentration ranging from 125 μg/ml to 500 μg/ml.

In another preferable embodiment of the present invention, the antigen has a concentration of 20 μg/ml, the aluminium adjuvant has a concentration of 125 μg/ml, 250 μg/ml, 300 μg/ml, 400 μg/ml or 500 μg/ml, and the CpG-ODN has a concentration of 125 μg/ml, 250 μg/ml or 500 μg/ml.

In a further preferable embodiment of the present invention, the antigen has a concentration of 20 μg/ml, the aluminium adjuvant has a concentration of 25 μg/ml, and the CpG-ODN has a concentration of 500 μg/ml. Alternatively, the antigen has a concentration of 20 μg/ml, the aluminium adjuvant has a concentration of 25 μg/ml, and the CpG-ODN has a concentration of 125 μg/ml. Alternatively, the antigen has a concentration of 20 μg/ml, the aluminium adjuvant has a concentration of 125 μg/ml, and the CpG-ODN has a concentration of 25 μg/ml. Alternatively, the antigen has a concentration of 20 μg/ml, the aluminium adjuvant has a concentration of 300 μg/ml, and the CpG-ODN has a concentration of 125 μg/ml. Alternatively, the antigen has a concentration of 20 μg/ml, the aluminium adjuvant has a concentration of 400 μg/ml, and the CpG-ODN has a concentration of 125 μg/ml. Alternatively, the antigen has a concentration of 20 μg/ml, the aluminium adjuvant has a concentration of 125 μg/ml, and the CpG-ODN has a concentration of 500 μg/ml.

The pharmaceutical composition of the present invention also comprises pharmaceutically acceptable excipients, which are selected from the group consisting of solvents, dispersion media, coating agents, surfactants, antioxidants, preservatives (e.g., antibacterial agents, antifungal agents), isotonic agents, absorption delaying agents, salts, drug stabilizers, binders, disintegration agents, lubricants, sweetening agents, flavoring agents, dyes, such like materials and combinations thereof.

In another aspect, the present invention provides use of the pharmaceutical composition of the present invention in manufacturing a medicament for inducing the immune response against an antigen in a subject. Using the excipients commonly used in pharmaceutical field, the pharmaceutical composition of the present invention can be formulated for parenteral administration, for example, for injectable administration, for oral administration such as tablets, pills, capsules, gels, syrups, slurries and suspensions, or for transdermal administration, or others commonly used in the art. In one embodiment of the present invention, the medicament for inducing immune response against an antigen in a subject, which is prepared from the pharmaceutical composition of the present invention, is Hepatitis B vaccines or Hepatitis C vaccines. Alternatively, the medicament for inducing immune response against an antigen in a subject, which is prepared from the pharmaceutical composition of the present invention, is genetic engineering Hepatitis B vaccines, including recombinant yeast-derived Hepatitis B vaccines and recombinant CHO-derived Hepatitis B vaccines.

In yet another aspect, the present invention provides a method for inducing immune response against an antigen in a subject, comprising administration of effective amount of the pharmaceutical composition of the present invention to the subject. The method also comprises re-administration of effective amount of the pharmaceutical composition of the present invention to the subject, wherein the interval time between administration and re-administration ranges from 2 to 12 weeks. In one embodiment of the present invention, the interval time between administration and re-administration is 4 weeks. Twice administration of the pharmaceutical composition of the present invention to a subject can induce immune response against an antigen in the subject, and thus produce protective antibody response level. It can be seen that the times for administration and the whole immune time for inducing immune response in a subject are decreased, in comparison with three-time administration for inducing immune response, which is commonly used in the art.

DETAILED DESCRIPTION OF THE INVENTION

Figure 1:
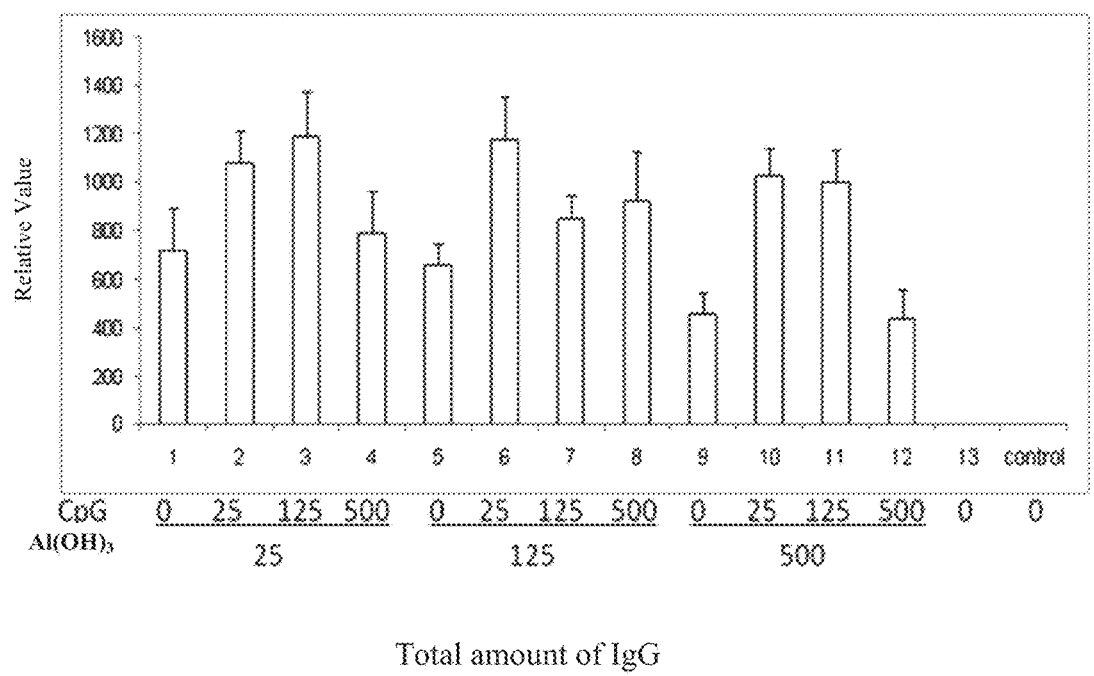
FIG. 1 shows variation on total amount of IgG, wherein CpG with different concentrations and aluminium adjuvant with different concentrations are used in combination to induce production of IgG from HBsAg.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Unless defined otherwise, all technical and scientific terms used herein generally have the same meaning as commonly understood by one of ordinary skill in the art to which this invention belongs.

Definition

Immune Adjuvant

The immune adjuvant of the present invention is an immune adjuvant well known by one having ordinary skill in the art, which can be grouped into (1) microorganism and the products thereof, wherein common microorganism includes *Mycobacterium, Corynbacterium parvum, Bordetella pertussis* and extracts of Gram-negative bacteria (i.e., lipopolysaccharide), extracts of *Mycobacterium* (i.e., muramyl dipeptide) and so on; (2) polynucleotide, such as polyinosinic acid:cytidylic acid (polyI:C), polyadenosinic acid (polyI:A: μ) and so on; (3) Freund adjuvant; (4) inorganic substances, such as alums and so on. The immune adjuvant plays its role depending on following mechanisms: (1) stimulating mononuclear-phagocyte system and thus enhancing capacity of this system for handling and presenting antigens; (2) extending the residence time of antigens in body, and thus increasing the opportunity for antigens to contact with immune cells; (3) inducing inflammatory response at antigen injection site and topical lymph node thereof and thus facilitating stimulation of proliferative effect of immune cells.

CpG Oligonucleotides (CpG-ODN)

CpG oligonucleotides of the present invention pertain to a novel immune adjuvant, which consist of unmethylated dinucleotide linked by phosphodiester bond and play a role in immune stimulation. CpG-ODN is able to facilitate proliferation and differentiation of B cells and secretion of IL-6 therefrom, thereby inducing secretion of antibodies. CpG-ODN is also able to activate antigen presenting cells such as mononuclear, macrophage, dendritic cells and the like, to secrete cytokines (such as IL-12, IL-6, TNF-α, IFN-α and IFN-β and the like). CpG-ODN indirectly enhances activity of cytotoxic T lymphocytes (CTL) and natural killer cells (NK) through cytokines, induces production of cell immune from intracellular pathogen and induces secretion of IFN-γ from NK cells and T cells. Besides inducing natural immune response, CpG-ODN can reinforce antigen-specificity response, due to (1) strong synergetic effect between signal transduction pathway resulting from B cells antigen receptor and B-cell signal transduction pathway resulting from CpG; (2) T helper Th1-like cytokines that is able to increase antigen specificity; and thereby enhancing antigen specificity reaction of B cells and T cells; and (3) positive regulation of co-stimulation molecules for cell reactions.

In 1890s, it was found that injection of extracts from bacteria to patients having cancers could relieve the patients' conditions. Researches revealed that bacteria DNAs have direct immune stimulation effect and anti-tumor effect later. It was found that immune stimulation effect of bacteria DNAs is associated with CpG unmethylated dinucleotide based on experiments with synthetic oligodeoxynucleotides.

CpG-ODN with immunostimulatory activity has basic structure with following features:
  a. CpG motifs are a basic structure for CpG-ODN to produce immune stimulation effect, which consists of CpG dinucleotide and two bases respectively located at 5' and 3' ends thereof.
  b. Purine and pyrimidine on both sides of CpG as well as space between CpGs will have influence on immunostimulatory activity of CpG-ODN and function thereof.
  c. It is optimal that ODN contains 2 to 4 CpG motifs and CpG motifs are normally spaced with at least two bases, most preferably, which is thymine.
  d. CpG-ODN containing poly-G sequence (consisting of three or more guanine) has strong function on stimulating plasmacytoid dendritic cells (pDC) to produce interferon-$\alpha$. Fully phosphorthioate-modified CpG-ODN is the most stable and has the best function on stimulating B cells. However, fully phosphorthioate-modified CpG-ODN is suboptimal for stimulating pDC to produce IFN-$\alpha$ in comparison with partially phosphorthioate-modified CpG-ODN.

Based on the function, CpG-ODN can be grouped into three types (Tomoki Ito, et al., Blood, 2006, Vol 107, Num 6: 2423-2431):
  (1). A type CpG-ODN: it is synthesized by chimeric backbones, in which 5' and 3' ends of the backbones is phosphorothioate, CpG area in the middle of the backbones is phosphodiester. Such ODN can well activate natural killer cells (NK cells) and plasmacytoid dendritic cells (pDC cells) to produce a great amount of IFN-$\alpha$, but has limitation to activate B cells;
  (2). B type CpG-ODN: it is synthesized by phosphorothioate backbone that is resistant to nuclease, it can activate B cells and pDC cells to produce IL-12 and induce secretion of antibodies, but such CpG-ODN has limitation to activate NK cells. Normally, B type CpG-ODN can be effectively used as vaccine adjuvant; and
  (3). C type CpG-ODN: it is synthesized by phosphorothioate backbone and has stimulatory activity between A type CpG-ODN and B type CpG-ODN. For example, C type CpG-ODN can not only well activate B cells, but also well activate NK cells and pDC cells.

CpG-ODN as used herein has a sequence of 5'-tcgacgt-tcgtcgttcgtcgttc-3' (SEQ ID NO.: 1). In one preferable embodiment of the present invention, the nucleotide sequence of CpG-ODN used in the present invention is 5'-tcgacgttcgtcgttcgtcgttc-3' (SEQ ID NO.: 1). The said CpG-ODN has a concentration ranging from 125 μg/ml to 500 μg/ml, or from 25 μg/ml to 125 μg/ml, or from 125 μg/ml to 250 μg/ml, or from 250 μg/ml to 500 μg/ml.

The bases contained in CpG-ODN of the present invention can be unmodified, partially modified, or fully modified. The modification may include one or more chemical modifications. For example, the bases contained in CpG-ODN of the present invention can be partially or fully modified by phosphorothioate. The modification can be done during synthesis or after synthesis of oligonucleotides and the modification can be occurred on phosphodiester bridge between nucleosides, ribose unit and/or natural nucleoside bases (adenine, guanine, cytosine and thymine). Under the circumstance that the modification is occurred during synthesis of oligonucleotides, the modified bases can be incorporated into oligonucleotides or located on the ends of oligonucleotides. Under the circumstance that the modification is occurred after synthesis of oligonucleotides, the modification can be done by using active groups, such as amino-modified component, 3' or 5' hydroxyl group, or phosphate group.

The chemical modification used in the present invention can include modification of CpG-ODN backbone of the present invention, including but not limited to modification of backbone with phosphorothioate and thereby obtaining phosphorothioate backbone. Such backbone is a stable nucleic acid molecular sugar-phosphate backbone, in which, on the bond of at least one nucleotide, oxygen in phosphate group that is not bridged is substituted by sulphur, alternatively, on the bond of each nucleotide or every other nucleotide, oxygen in phosphate group that is not bridged is substituted by sulphur. Other modifications can be occurred on oligonucleotide backbones. For example, oligonucleotide backbones can be modified by non-ionic DNA analogues, for example the backbone can be modified by alkyl phosphate and aryl phosphate, in which, oxygen in charged phosphate group can be substituted by alkyl or aryl, or the backbone can be modified by phosphodiester and alkyl phosphotriester, in which the charged oxygen can be alkylated.

Aluminium Adjuvant

The aluminium adjuvant used in the present invention is an immune adjuvant well known and commonly used in the art, which can strongly adsorb protein antigen from solution, so as to form precipitates. After inoculating such aluminium adjuvant in the body, it can form an antigen reservoir to gradually release antigen, thereby fully extending the action time for an antigen. Meanwhile, the aluminium adjuvant can facilitate topical (injection site) macrophage response. The aluminium adjuvant of the present invention is selected from the group consisting of aluminium hydroxide, aluminium phosphate and aluminium sulfate.

In the preferable embodiment of the present invention, the aluminium adjuvant is aluminium hydroxide ($Al(OH)_3$). The aluminium adjuvant has a concentration ranging from 25 μg/ml to 125 μg/ml, or from 125 μg/ml to 500 μg/ml, or from 125 μg/ml to 400 μg/ml, or from 125 μg/ml to 300 μg/ml, or from 250 μg/ml to 500 μg/ml, or from 300 μg/ml to 400 μg/ml, or from 400 μg/ml to 500 μg/ml, or from 300 μg/ml to 500 μg/ml.

Antigen

The antigen of the present invention refers to substances that are able to induce immune response in immune system of the body and combine in vivo or in vitro with products (antibodies and/or effector cells) from immune response so as to result in specificity reaction. The antigen may include proteins, lipids, sugars, nucleic acids, chemical compounds and the like, in which, the proteins as antigens may include modified or unmodified proteins. The modification may include glycosylation or methylation, for example, the proteins can be cyclized or connected to lipids. Antigens associated with an infectious agents or diseases may include antigens that are part of the infectious agent, such as envelope proteins, capsid proteins, surface proteins, toxins, cell walls, antigenic lipids, and the like. Other suitable antigens may include antigens of the host, including those that are induced, modified or otherwise overexpressed as a marker of infection or disease. All such antigens that are derived from, or associated with, an infectious agent, an infection, a condition or disease, are suitable for use in the present invention.

In some embodiments of the present invention, the antigen is a virus-related antigen. The virus includes but not limited to hepatitis virus, such as hepatitis B virus, hepatitis C virus.

Hepatitis B Surface Antigen (HBsAg)

The hepatitis B surface antigen of the present invention consists of 226 amino acid residues, including three protein components: small molecule S protein, middle molecule M protein and large molecule L protein. These three protein components share a common C end. S area is divided into three sections: S gene, preS1 gene and preS2 gene. These three sections have the same reading frame phase, continuously arrange in series, and respectively encode S protein, preS1 protein and preS2 protein. The products encoded in S gene area not only act as a major component in assembly of virus and subvirus particles, but also stimulate organism to produce neutrality antibody (a.k.a. protective antibody). Previously, it was believed that only S protein can stimulate organism to produce neutrality antibody. Recent researches reveal that polypeptides of preS1 and preS2 have strong immunogenicity and contain multiple advantageous antigen determinants. T-cell immune response caused by preS antigen can help certain individuals to overcome the condition that no immune response to S protein or no immune response to both S protein and preS2 protein occurs in the individuals. Hepatitis B surface antigen (HBsAg) has 14 cysteine (Cys) residues which form complicated spatial structure with disulfide bond of Cys. In terms of serology, HBsAg can be divided into four major subtypes: adr, adw, ayr and ayw. Common antigen a determinants are located on 124-147 amino acid residues of S protein, and form hydrophilic bicyclic structure. Such configuration is closely associated with antigenicity of a determinants and also has critical correlation with immunogenicity. Hepatitis B surface antigen (HBsAg) is an external capsid protein of hepatitis B virus, which is not an intact virus. Such surface antigen contains no virus genetic materials and has no infectivity and pathogenicity, but retains immunogenicity. That is to say, such surface antigen retains capacity for stimulation of organism to produce protective antibody. Previously, hepatitis B surface antigen is extracted from the blood of hepatitis B virus carriers, and then such antigen is subject to strict procedures such as purification and inactivation and the like, so as to prepare haematogenous hepatitis vaccine. However, such vaccine is eliminated due to safety, source and cost and the like (for example, such vaccine has high risk of causing haematogenous diseases and preparation of such vaccine wastes large amount of plasma).

In the preferable embodiment of the present invention, the antigen is hepatitis B surface antigen. The antigen has a concentration ranging from 1 µg/ml to 100 µg/ml, or from 5 µg/ml to 100 µg/ml, or from 10 µg/ml to 100 µg/ml, or from 15 µg/ml to 100 µg/ml, or from 20 µg/ml to 100 µg/ml, or from 1 µg/ml to 90 µg/ml, or from 1 µg/ml to 80 µg/ml, or from 1 µg/ml to 70 µg/ml, or from 1 µg/ml to 60 µg/ml, or from 1 µg/ml to 50 µg/ml, or from 1 µg/ml to 40 µg/ml, or from 1 µg/ml to 30 µg/ml, or from 1 µg/ml to 20 µg/ml.

Concentration

Each component contained in the pharmaceutical composition of the present invention has a concentration that is sufficient to induce immune response in the immune system of individual. The concentration of each component contained in the pharmaceutical composition of the present invention depends on factors such as the specific immune adjuvant used in the composition and the activity of antigen, administration route, other components used in combination, severity of the specific disease being treated or prevented, dosage form and the like. The concentration of each component contained in the pharmaceutical composition of the present invention is an optimal concentration for safety and efficiency. Typically, dosage-efficiency relationship obtained via in vivo and/or in vitro experimentation can provide a guideline for determination of concentration of each component contained in the pharmaceutical composition.

In accordance with the preferable embodiment of the present invention, in the pharmaceutical composition of the present invention, the antigen has a concentration of 20 µg/ml, the aluminium adjuvant has a concentration ranging from 250 µg/ml to 500 µg/ml or from 300 µg/ml to 500 µg/ml, and the CpG-ODN has a concentration ranging from 125 µg/ml to 500 µg/ml. More preferably, the antigen has a concentration of 20 µg/ml, the aluminium adjuvant has a concentration of 125 µg/ml, 250 µg/ml, 300 µg/ml, 400 µg/ml or 500 µg/ml, and the CpG-ODN has a concentration of 125 µg/ml, 250 µg/ml or 500 µg/ml.

In accordance with another preferable embodiment of the present invention, in the pharmaceutical composition of the present invention, the antigen has a concentration of 20 µg/ml, the aluminium adjuvant has a concentration of 25 µg/ml, and the CpG-ODN has a concentration of 500 µg/ml; or the antigen has a concentration of 20 µg/ml, the aluminium adjuvant has a concentration of 25 µg/ml, and the CpG-ODN has a concentration of 125 µg/ml; or the antigen has a concentration of 20 µg/ml, the aluminium adjuvant has a concentration of 125 µg/ml, and the CpG-ODN has a concentration of 25 µg/ml; or the antigen has a concentration of 20 µg/ml, the aluminium adjuvant has a concentration of 300 µg/ml, and the CpG-ODN has a concentration of 125 µg/ml; or the antigen has a concentration of 20 µg/ml, the aluminium adjuvant has a concentration of 400 µg/ml, and the CpG-ODN has a concentration of 125 µg/ml; or the antigen has a concentration of 20 µg/ml, the aluminium adjuvant has a concentration of 125 µg/ml, and the CpG-ODN has a concentration of 500 µg/ml.

Pharmaceutically Acceptable Excipient

In addition to antigen, CpG oligonucleotide with a sequence of 5'-tcgacgttcgtcgttcgtcgttc-3' and aluminium adjuvant, the pharmaceutical composition can comprise pharmaceutically acceptable excipients. The pharmaceutically acceptable excipients of the present invention include solvents, dispersion media, coating agents, surfactants, antioxidants, preservatives (e.g., antibacterial agents, antifungal agents), isotonic agents, absorption delaying agents, salts, drug stabilizers, binders, disintegrants, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference).

Examples of filling agents are lactose monohydrate, lactose anhydrous and various starches; examples of binding agents are various celluloses and cross-linked polyvinylpyrrolidone, microcrystalline cellulose and siliconized microcrystalline cellulose. Suitable lubricants include agents that act on the flowability of the powder to be compressed, such as colloidal silicon dioxide, stearic acid, magnesium stearate, calcium stearate and silica gel. Examples of sweetening agents are any natural or artificial sweetening agents, such as sucrose, xylitol, sodium saccharin, cyclamate and aspartame. Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride. Examples of suitable diluents include pharmaceutically acceptable inert fillers, such as microcrystalline cellulose, lactose, dibasic calcium phosphate and saccharides. Examples of diluents include microcrystalline cellulose, lactose such as lactose monohydrate and lactose anhydrous, dibasic calcium phosphate, mannitol, starch, sorbitol, sucrose and glucose. Suitable disintegrants include lightly cross-linked polyvinylpyrrolidone, corn starch, potato starch, maize starch and modified starch, cross-linked polyvinylpyrrolidone, sodium starch glycolate and mixtures thereof.

Dosage Form

The pharmaceutical composition of the present invention can be in the form of aqueous solution, saline solution, particles, aerosols, powders, tablets, dragees, microcapsules, suppositories, syrups, lotions, suspensions, creams, drops or other forms suitable for a variety of pharmaceutical delivery system.

The pharmaceutical composition of the present invention can be formulated for oral, parenteral, sublingual, transmucosal, transdermal, rectal, intraperitoneal, subcutaneous, intramuscular, intravenous, intraarterial, intrathecal, topical (topical administration in the form of powders, ointments, gels, drops or transdermal patches), buccal, through catheter, through implant administration, and the like. No matter what kind of administration route is used, the pharmaceutical composition must be sterilized and stable under manufacture and storage condition, and will not be polluted by bacteria or microorganism.

The pharmaceutical composition of the present invention can be formulated for parenteral administration through injection (e.g., bolus injection or continuous infusion). The injectable dosage form can be provided in unit dose, such as in the form of ampoule or multiple doses container. The pharmaceutical composition of the present invention can be in the form of suspensions, solutions or emulsions in lipophilic or hydrophilic carriers and may contain regulators such as suspending agents, stabilizing agents and/or dispersions. And for example, cross-linked polyvinylpyrrolidone, agar or alginic acid or its salt (such as sodium alginate) can be added to the pharmaceutical composition of the present invention.

Suspensions of the pharmaceutical composition of the present invention may be prepared as appropriate lipophilic or hydrophilic injection suspensions. Suitable lipophilic solvents or vehicles include fatty oils such as sesame oil, or synthetic fatty acid esters, such as ethyl oleate or triglycerides, or liposomes. Hydrophilic injection suspensions may contain substances which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the pharmaceutical composition of the invention may be formulated as aqueous solutions, preferably as physiologically compatible buffers such as Hanks's solution, Ringer's solution, or physiological saline buffer solution.

Preferably, the pharmaceutical composition of the present invention may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For buccal administration, the pharmaceutical composition of the present invention may take the form of tablets or lozenges formulated in conventional manner.

For administration by inhalation, the pharmaceutical composition of the present invention can be formulated for convenient delivery in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the pharmaceutical composition of the present invention and a suitable powder base such as lactose or starch.

The pharmaceutical composition of the present invention also may comprise suitable solid or gel phase carriers or excipients. Examples of such carriers or excipients include calcium carbonate, calcium phosphate, various sugars, starches, cellulose derivatives, gelatin, and polymers such as polyethylene glycols.

Vaccine

The vaccine of the present invention refers to a preparation designed to induce an immune response against an antigen. The vaccine may be therapeutic, given during treatment to boost the immune response or drive the response in a specific direction, or it may be prophylactic or preventative, given prior to or shortly after exposure to a disease. The vaccine may be both therapeutic and prophylactic at the same time, in treating an existing condition and preventing future recurrences. The vaccine can be administrated to a subject through common route in the art. The term "administration" as used herein encompasses all suitable means of providing a substance to a patient. Common routes include oral, sublingual, transmucosal, transdermal, rectal, vaginal, subcutaneous, intramuscular, intravenous, intraarterial, intrathecal, via catheter, via implant etc.

The pharmaceutical composition of the present invention can be used to prepare a medicament for inducing immune response against an antigen in a subject. In one embodiment, the pharmaceutical composition of the present invention can be used to prepare a hepatitis B or hepatitis C vaccine. In the preferable embodiment of the present invention, the pharmaceutical composition of the present invention can be used to prepare a genetic engineering Hepatitis B vaccine, such as recombinant yeast-derived Hepatitis B vaccine and recombinant CHO-derived Hepatitis B vaccine. The genetic engineering Hepatitis B vaccine is prepared by constructing the gene of hepatitis B virus surface antigen on an expression vector, using DNA recombination technology, then transfecting into host yeast cells or mammal cells to express therein, next assembling or secreting HBsAg during in vitro culture and proliferation, followed by combining with the aluminium adjuvant and CpG of the present invention, finally separation and purification. Depending on different host cells into which the gene of hepatitis B virus surface antigen is transfected, various genetic engineering Hepatitis B vaccines can be obtained. For example, in the case that the host cells are yeast cells (such as Brewer's yeast or *Hansenula* yeast cells), a recombinant yeast-derived Hepatitis B vaccine can be obtained; in the case that host cells are Chinese hamster ovary cells (CHO cells), a recombinant CHO-derived Hepatitis B vaccine can be obtained.

Medical Use

The pharmaceutical composition of the present invention can be used to induce immune response against an antigen in a subject, including administrating effective amount of the pharmaceutical composition of the present invention to the subject, and further including re-administrating effective amount of the pharmaceutical composition of the present invention to the subject, wherein the interval time between administration and re-administration can be 2, 3, 4, 5, 6, 7, 8, 9, 10, 11 or 12 weeks, and the re-administration can be carried out in the same or different administration route at the same or different amount. Twice administration can induce immune response against an antigen in the subject, thereby producing protective antibody response level. Comparing with the current three-time administration to induce immune response, twice administration has decreased administration times and shortened the whole immune time for inducing immune response in the subject.

In one preferable embodiment of the present invention, the immune response against an antigen in the subject can be induced by administration of effective amount of the pharmaceutical composition of the present invention to the subject at 0 time and then administration of effective amount of the pharmaceutical composition of the present invention to the subject at 4 weeks by the same administration route. The pharmaceutical composition of the present invention with pharmaceutically acceptable carriers together can be administrated to the subject. For example, the pharmaceutical composition of the present invention can be administrated to the subject in the form of sterile pyrogen-free saline solution, sterile pyrogen-free saline suspension. The pharmaceutically acceptable carriers refer to one or more solid or liquid fillers, diluents or encapsulating materials, which are suitable for administrating the pharmaceutical composition of the present invention to the subject. The said carriers can be organic, inorganic, natural or synthetical materials. The said carriers include any and all solutions, diluents, solvents, dispersion media, liposomes, emulsions, coating agents, antibacterial agents and antifungal agents, isotonic agents, absorption delaying agents and any other carriers that are suitable for administrating the pharmaceutical composition of the present invention to the subject. The pharmaceutically acceptable carriers can be selected depending on specific administration route. Parental formulation typically includes injectable liquid that includes pharmaceutically and physiologically acceptable liquid, such as water, physiological saline solution, balanced salt solution, glucose solution, glycerine, etc. For solid composition (such as powders, pills, tablets or capsules), the composition may comprise trace non-toxic adjuvants, such as wetting agents or emulsifying agents, preservatives and pH buffers, etc.

The effective amount as used herein refers to effective dose of the pharmaceutical composition of the present invention, which is sufficient to induce immune response against an antigen in a subject. Such effective dose can be determined by one having ordinary skill in the art according to the common knowledge in the art. For example, the said effective dose can be determined by one having ordinary skill in the art, depending on various factors such as age, gender, body weight of the subject, administration route, type of immune response to be induced. And the said effective dose can be determined from animal models. For example, the effective dose in humans can be adjusted by determining the dose that achieves effective induction of immune response against an antigen in animal models such as mice models. The said effective dose can also be determined from human data of pharmaceutical composition which are known to exhibit similar pharmacological activities. For example, in the case of administration of the pharmaceutical composition of the present invention through injection, the effective dose normally can be varied from about 0.01 mg/kg/person to 150 mg/kg/person.

Subject

As used herein, the term "subject" refers to animal, including but not limited to, primates (e.g., humans), cows, sheep, goats, horses, dogs, cats, rabbits, rats, mice, fish, birds, and the like. In a preferable embodiment, the subject is human.

Immune Cells

As used herein, "immune cell" refers to all cells that are involved in the immune response and associated with immune response, and precursor cells thereof. The immune cells include T cells such as CD4+ cells, CD8+ cells and various other T cell subsets, B cells, natural killer cells (NK cells), macrophages, monocytes, dendritic cells, and neutrophils.

Specific T lymphocytes and specific B lymphocytes expressing specific antigen receptors involve in mediation of acquired immune response, in which B lymphocytes can be activated, proliferated and differentiated into plasmocytes after applying antigen specificity stimulation thereto, and then specific antibodies are produced, which can mediate humoral immune response. T lymphocytes can be activated, proliferated and differentiated into effector T cells after applying antigen specificity stimulation thereto, and then cell immune response is mediated, which aids humoral immune response. In addition, professional antigen presentation cells (APC) such as dendritic cells, mononuclear macrophages and the like involve in initiation stage of acquired immune response to present antigen and activate T cells. Mononuclear macrophages and NK cells, collaborating with T cells and antibodies and the like, involve in effective stage of acquired immune response to play a role in cleaning antigen.

Cells involving in innate immune response are mononuclear macrophages, granulocytes, dendritic cells, NK cells, endothelial cells, mastocytes, red blood cells, blood platelets and the like and minority of subgroup of T lymphocytes and B lymphocytes, among which, NK cells are the third type of lymphocytes, having non-specific cell cytotoxic activity, playing a critical role in innate immune response, anti-virus infection and anti-tumor. Mononuclear macrophages and granulocytes have strong function on phagocytosis and killing, and they involve in inflammatory reaction through releasing a large amounts of active products.

The pharmaceutical composition of the present invention exhibits synergistic effect with aluminium adjuvant and CpG oligonucleotides to induce humoral and cell immune response at the same time, thereby boosting immune function of Th1-type T cells and greatly enhancing T cell immune response.

EXAMPLES

Example 1: Pharmaceutical Composition Comprising Hepatitis B Surface Antigen (HBsAg) and Aluminium Hydroxide as Well as CpG Oligonucleotides This example 1 provides a pharmaceutical composition comprising hepatitis B surface antigen (HBsAg) and aluminium hydroxide as well as CpG oligonucleotides, in which hepatitis B surface antigen (HBsAg) and aluminium hydroxide as well as CpG oligonucleotides have various concentrations as listed respectively in Table 1.

TABLE 1

| Number# | HBsAg (µg/ml) | Al(OH)$_3$ (µg/ml) | CpG (µg/ml) |
|---|---|---|---|
| 1# | 20 | 25 | 0 |
| 2# | 20 | 25 | 25 |

TABLE 1-continued

| Number# | HBsAg (µg/ml) | Al(OH)₃ (µg/ml) | CpG (µg/ml) |
|---|---|---|---|
| 3# | 20 | 25 | 125 |
| 4# | 20 | 25 | 500 |
| 5# | 20 | 125 | 0 |
| 6# | 20 | 125 | 25 |
| 7# | 20 | 125 | 125 |
| 8# | 20 | 125 | 500 |
| 9# | 20 | 500 | 0 |
| 10# | 20 | 500 | 25 |
| 11# | 20 | 500 | 125 |
| 12# | 20 | 500 | 500 |
| 13# | PBS | PBS | PBS |

To detect the function of the pharmaceutical composition comprising HBsAg and Al(OH)₃ as well as CpG-ODN with various concentrations thereof as listed respectively in Table 1 mentioned above of this example 1 on induction of IgG, IgG2a and IgG1, the following methods are performed.

1.1 Reagents:
(1) Hepatitis B surface antigen (HBsAg, without aluminium adjuvant, purchased from National Vaccine & Serum Institute);
(2) Goat anti-mouse IgG2a and IgG1 labelled by horse radish peroxidase (HRP) (purchased from Serotec company);
(3) PBS solution: prepared by completely dissolving 8 g NaCl (purchased from Beijing Chemical Factory), 0.2 g KCl (purchased from Beijing Chemical Factory), 2.9 g Na₂HPO₄.12H₂O (purchased from Beijing Chemical Factory), 0.2 g KH₂PO₄ (purchased from Beijing Chemical Factory) in 800 ml ultrapure water, and then adjusting pH between 7.2 to 7.4 with HCl or NaOH;
(4) coating solution: prepared with 80 ml PBS solution;
(5) scrubbing solution: prepared with 400 ml PBS and 0.5 ml Tween 20 (purchased from Beijing Chemical Factory);
(6) blocking solution: prepared with 80 ml PBS and 1 g bovine serum albumin (BSA, purchased from Beijing Dingguo Biological Technology LTD.);
(7) sample diluent solution: prepared by dissolving 2.42 g Tris (purchased from Beijing Chemical Factory) and 8.77 g NaCl (purchased from Beijing Chemical Factory) in 800 ml ultrapure water and adjusting pH to 7.1 with HCl, then adding 1 g BSA and 0.5 ml Tween 20 thereto;
(8) substrate solution: prepared by mixing 19.2 g aqueous solution of citric acid (purchased from Beijing Chemical Factory) and 71.1 g aqueous solution of Na₂HPO₄.12H₂O (purchased from Beijing Chemical Factory), and then filtering through 0.22 µm membrane;
(9) stop solution: prepared by dilute sulphuric acid;
(10) CpG-ODN (5'-tcgacgttcgtcgttcgtcgttc-3', SEQ ID NO. 1, purchased from Beijing DNA Biotechnology Co., Ltd.) solution: prepared by dissolving various amount of CpG-ODN in sterile physiological saline solution;
(11) Al(OH)₃ (purchased from Beijing Chemical Factory) solution: prepared by dissolving various amount of Al(OH)₃ in sterile physiological saline solution.

1.2 Method:
100 µl HBsAg (5 µg/ml) was added to 10 ml coating solution to dilute HBsAg, and then the diluted HBsAg was added to respective wells of ELISA plate, standing at 4° C. overnight. Next day, ELISA plate was taken out, the liquid in respective wells of ELISA plate was sucked out and then 300 µl scrubbing solution was added to the plate, standing in room temperature for 3 min, repeated three times. Then 300 µl blocking solution was added to respective wells, standing in room temperature for 1 hour, followed by washing the plate. Then Al(OH)₃ solution with different concentrations and CpG-ODN solution with different concentrations were added to respective wells of ELISA plate (the concentrations of Al(OH)₃ solution and CpG-ODN solution are listed in Table 1). Next, goat anti-mouse IgG2a and IgG1 labelled by HRP and diluted by sample diluent solution (dilution ratio 1:100000) was added to respective wells, standing in room temperature for 1 hour without exposure to the light. 100 µl substrate solution then was added to respective wells of ELISA plate, incubating in room temperature for 10-20 min without exposure to the light, followed by adding 50 µl stop solution thereto. Within 5 min since adding stop solution, 450 nm absorbency was measured by ELISA instrument.

1.3 Results:
As shown in FIG. 1 (control refers to blank sample), under the condition that aluminium hydroxide has concentrations of 25 µg/ml, 125 µg/ml and 500 µg/ml, CpG-ODN with a concentration ranging from 25 to 500 µg/ml will significantly induce production of IgG. Under the condition that aluminium hydroxide has a concentration of 25 µg/ml and CpG-ODN has a concentration of 125 µg/ml and under the condition that aluminium hydroxide has a concentration of 125 µg/ml and CpG-ODN has a concentration of 25 µg/ml, aluminium hydroxide in combination with CpG-ODN induces production of maximum amount of IgG. Moreover, the amount of IgG produced by CpG-ODN in combination with aluminium hydroxide is higher than the amount of IgG produced by aluminium hydroxide alone. And the amount of IgG produced by CpG-ODN with low to medium concentration (25 to 125 µg/ml) in combination with aluminium hydroxide is slightly higher than the amount of IgG produced by CpG-ODN with high concentration (higher than 125 µg/ml) in combination with aluminium hydroxide.

Figure 2:
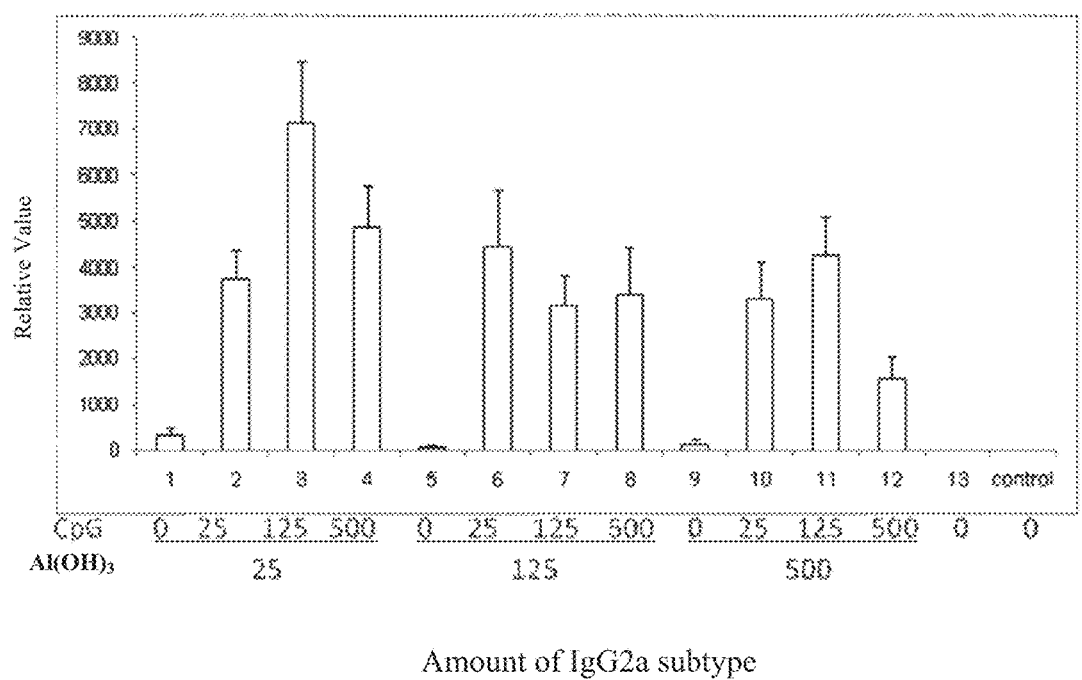
FIG. 2 shows variation on amount of IgG2a subtype, wherein CpG with different concentrations and aluminium adjuvant with different concentrations are used in combination to induce production of IgG2a subtype from HBsAg.

As shown in FIG. 2 (control refers to blank sample), under the condition that aluminium hydroxide has concentrations of 25 µg/ml, 125 µg/ml and 500 µg/ml respectively, CpG-ODN with a concentration ranging from 25 to 500 µg/ml is able to significantly increase the amount of IgG2a antibody. And under the condition that aluminium hydroxide has a concentration of 25 µg/ml and CpG-ODN has a concentration of 125 µg/ml, the amount of IgG2a antibody is the highest, next is the condition that aluminium hydroxide has a concentration of 25 µg/ml and CpG-ODN has a concentration of 500 µg/ml, and the condition that aluminium hydroxide has a concentration of 125 µg/ml and CpG-ODN has a concentration of 25 µg/ml, as well as the condition that aluminium hydroxide has a concentration of 500 µg/ml and CpG-ODN has a concentration of 125 µg/ml. It can be seen from FIG. 2 that combination of CpG-ODN and aluminium hydroxide is able to significantly increase the amount of IgG2a antibody. Through variance analysis, it can be found that the amount of IgG2a antibody produced by CpG-ODN in combination with aluminium hydroxide has significant difference, comparing with the amount of IgG2a antibody produced by aluminium hydroxide alone ($P<0.05$). This indicates that production of IgG2a antibody can be greatly facilitated by combination of CpG-ODN and aluminium hydroxide, meanwhile T cell reaction is also facilitated.

Figure 3:
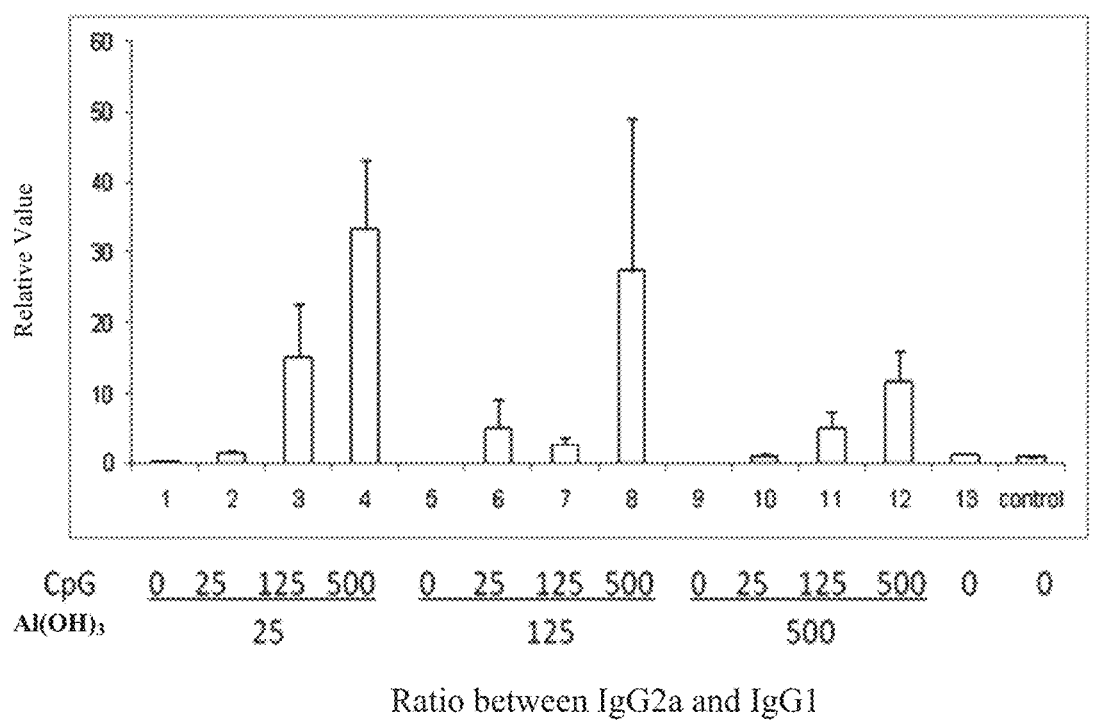
FIG. 3 shows variation on ratio between IgG2a and IgG1, wherein CpG with different concentrations and aluminium adjuvant with different concentrations are used in combination to induce production of IgG2a and IgG1 from HBsAg.

As shown in FIG. 3 (control refers to blank sample), under the condition that aluminium hydroxide has concentrations of 25 µg/ml, 125 µg/ml and 500 µg/ml respectively, CpG-ODN with a concentration ranging from 25 to 500 µg/ml is able to significantly increase IgG2a/IgG1 ratio. Under the condition that aluminium hydroxide has a concentration of 25 µg/ml and CpG-ODN has a concentration of 500 µg/ml, IgG2a/IgG1 ratio is the highest, next is the condition that aluminium hydroxide has a concentration of 125 µg/ml and CpG-ODN has a concentration of 500 µg/ml. This further indicates that CpG-ODN facilitates production of IgG2a antibody and inhibits production of IgG1 antibody, and combination of CpG-ODN and aluminium hydroxide can boost T cell immune response.

From FIGS. 1 to 3, it can be seen that under the condition that CpG-ODN has a concentration ranging from 25 to 500 µg/ml, reduction of the amount of aluminium hydroxide will not lead to reduction of total IgG level. Under the condition that aluminium hydroxide has a concentration of 25 µg/ml, there is no decline in Th1 type T cell immune function (using IgG2a/IgG1 ratio as indicator). This shows that Th1 is mainly influenced by CpG-ODN and there is a concentration dependent relationship between Th1 type T cell immune function and CpG-ODN.

Example 2: Induction of Antibodies to Produce Immune Response by the Pharmaceutical Composition Comprising Hepatitis B Surface Antigen (HBsAg) and Aluminium Hydroxide as Well as CpG Oligonucleotides This example 2 provides a pharmaceutical composition comprising hepatitis B surface antigen (HBsAg) and aluminium hydroxide as well as CpG oligonucleotides, with various concentrations thereof as listed respectively in Table 2.

TABLE 2

| Number# | HbsAg (µg/ml) | Al(OH)$_3$ (µg/ml) | CpG (µg/ml) |
|---|---|---|---|
| 1# | 20 | 300 | 125 |
| 2# | 20 | 300 | 250 |
| 3# | 20 | 300 | 500 |
| 4# | 20 | 400 | 125 |
| 5# | 20 | 400 | 250 |
| 6# | 20 | 400 | 500 |
| 7# | 20 | 500 | 125 |
| 8# | 20 | 500 | 250 |
| 9# | 20 | 500 | 500 |
| 10# | 20 | 500 | PBS |

To detect the function of the pharmaceutical composition comprising HBsAg and Al(OH)$_3$ as well as CpG-ODN with various concentrations thereof as listed respectively in Table 2 mentioned above of this example 2 on induction of antibodies to produce immune response, the following methods are carried out.

2.1 Materials and Reagents:

Animals for experimentation: clean degree BALB/C female mice, 4 to 6 weeks old (purchased from Vital River Laboratory Animal Technology Co. Ltd.), body weight: 15-25 g.

HBsAg stock (without aluminium adjuvant, purchased from National Vaccine & Serum Institute): prepared by dissolving 1 mg HBsAg protein lyophilized powder in 1 ml PBS for use.

CpG-ODN (5'-tcgacgttcgtcgttcgtcgttc-3', SEQ ID NO. 1, purchased from Beijing DNA Biotechnology Co., Ltd.) solution: prepared by dissolving various amount (see, the concentrations of CpG-ODN are listed in Table 2) of CpG-ODN in sterile physiological saline solution, one day before use, standing at 4° C. overnight for use.

Al(OH)$_3$ (purchased from Beijing Chemical Factory) solution: prepared by dissolving various amount of Al(OH)$_3$ in sterile physiological saline solution (the concentrations of Al(OH)$_3$ are listed in Table 2).

2.2 Methods:

50 µl solution of mixture comprising CpG-ODN solution, aluminium hydroxide solution and HBsAg solution with various concentrations was placed on ice for 10 min and then diluted. 100 µl diluted sample (containing 1 µg hepatitis B surface antigen) was injected into left anterior tibialis of female BALB/C mice (4 to 5 weeks old, 8 mice per group). The mice were immunized at 0 week and 4 weeks. At 2, 4, 6, 8 and 10 weeks, blood samples were collected from caudal vein, and at 12 weeks, the mice were euthanized and whole blood was collected. Basal serum was obtained on 5 days prior to immunization. The levels of anti-HBs in the serum of the mice before immunization and 2, 4, 6, 8 and 10 weeks after immunization were detected by using hepatitis B surface antibody kit.

Figure 4:
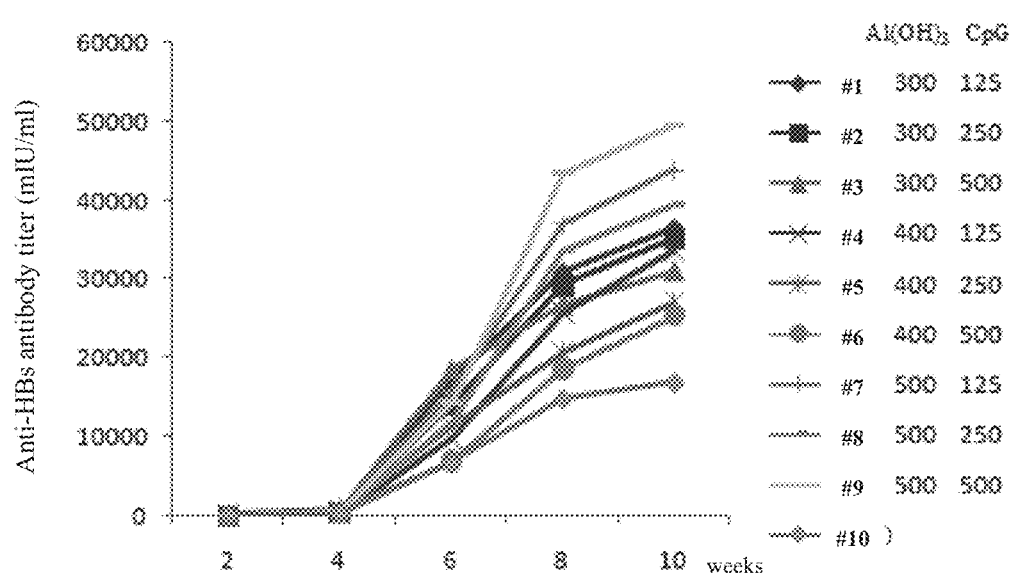
FIG. 4 shows variation on anti-HBs antibody titer, wherein CpG with different concentrations and aluminium adjuvant with different concentrations are used in combination to induce production of anti-HBs antibody in mice from HBsAg.

2.3 Results:

As shown in FIG. 4, the results from antibody detection show that the hepatitis B vaccine, comprising both CpG-ODN and aluminium hydroxide as adjuvants can induce high titer of anti-HBs at 6 to 8 weeks after immunization, and antibody titer increases over time until 10 weeks to increase gently. This indicates that the vaccines comprising both CpG-ODN and aluminium hydroxide as adjuvants have better immunogenicity than control vaccines (10#, only comprising Al(OH)$_3$ as adjuvant), which can rapidly produce protective antibody and make the antibody maintain at high level over time.

CpG-ODN and aluminium hydroxide have synergistic effect, both of which can be used in combination to increase vaccine-induced anti-HBsAg antibody response level. The vaccine comprising these two adjuvants has advantageous over the vaccine only comprising aluminium hydroxide.

During induction of immune response in the organism, the concentration of CpG-ODN and Al(OH)$_3$ as adjuvants has correlation with serum antibody titer, both of which exhibit synergistic effect on stimulation of humoral immune.

Example 3: Synergistic Effect Produced by Aluminium Hydroxide and CpG Oligonucleotides at Various Concentrations This example 3 provides a pharmaceutical composition comprising hepatitis B surface antigen (HBsAg) and aluminium hydroxide as well as CpG oligonucleotides, with various concentrations as listed respectively in Table 3.

TABLE 3

| Number# | HBsAg (µg/ml) | Al(OH)$_3$ (µg/ml) | CpG (µg/ml) |
|---|---|---|---|
| 1# | 20 | 300 | 125 |
| 2# | 20 | 300 | 250 |
| 3# | 20 | 300 | 500 |
| 4# | 20 | 400 | 125 |
| 5# | 20 | 400 | 250 |
| 6# | 20 | 400 | 500 |
| 7# | 20 | 500 | 125 |
| 8# | 20 | 500 | 250 |
| 9# | 20 | 500 | 500 |
| 10# | 20 | 500 | PBS |

In order to detect the synergistic effect produced by double adjuvants in the pharmaceutical composition comprising HBsAg and Al(OH)$_3$ as well as CpG-ODN with various concentrations thereof as listed respectively in Table 3 mentioned above of this example 3, the following methods are carried out.

3.1 Materials and Reagents:

Animals for experimentation: clean degree BALB/C female mice, 4 to 6 weeks old (purchased from Vital River Laboratory Animal Technology Co. Ltd.), body weight: 15 to 25 g.

HBsAg stock (without aluminium adjuvant, purchased from National Vaccine & Serum Institute): prepared by dissolving 1 mg HBsAg protein lyophilized powder in 1 ml PBS for use.

CpG-ODN (5'-tcgacgttcgtcgttcgtcgttc-3', SEQ ID NO. 1, purchased from Beijing DNA Biotechnology Co., Ltd.) solution: prepared by dissolving various amount (see, the concentrations of CpG-ODN are listed in Table 3) of CpG-ODN in sterile physiological saline solution, one day before use, standing at 4° C. overnight for use.

Al(OH)$_3$ (purchased from Beijing Chemical Factory) solution: prepared by dissolving various amount of Al(OH)$_3$ in sterile physiological saline solution (the concentrations of Al(OH)$_3$ are listed in Table 3).

3.2 Method:

50 μl solution of mixture comprising CpG-ODN solution, aluminium hydroxide solution and HBsAg solution with various concentrations was placed on ice for 10 min, then was serially diluted according to the ratios as listed in Table 4. Each mixture solution with different dilutions as listed in Table 4 was inoculated into BALB/c female mice (10 mice, 4 to 6 weeks old, body weight 14 g to 16 g). 1.0 ml mixture solution was injected into each mouse. After feeding the mice for 4 to 6 weeks, 1 ml blood sample was withdrawn from eyeballs of mice. The blood sample was placed at room temperature for more than 1 hour and then centrifuged for 2 min at 8000 rpm/min, thereby obtaining immunized serum. According to the manufacturer's instruction, hepatitis B surface antigen kit was used to detect anti-HBs as follows.

One blank control, 5 negative controls and 2 positive controls were prepared. 50 μl immunized serum to be detected as well as negative and positive control serums was added to each well respectively. Except the well containing blank control, 50 μl enzyme conjugate was added to each well and mixed gently. The plate was blocked and incubated for 30 min at 37° C. The plate was washed, and the liquid in each well was discarded. 350 μl scrubbing solution was added to plate to wash the plate for 5 times. After washing the plate at last time, the plated was dried gently. 50 μl developing agent was added to each well and mixed gently, then the plate was blocked. The developing agent was incubated for 15 min at 37° C. Next, 50 μl stop solution was added to each well and mixed gently. Absorbency at 450 nm (reference wavelength=630 nm) was detected by ELISA instrument (reading the value within 10 min after termination of reaction). The blank control was used for calibration. Average absorbency of negative control (NCX) was calculated. Critical value=average absorbency of negative control (NCX)×2.1 (if absorbency of negative control is below 0.05, 0.05 was used for calculation; if absorbency of negative control is above 0.05, real absorbency was used for calculation). Absorbency of each well was compared with critical value. If the absorbency is not less than the critical value, then the sample was considered as positive sample. Antibody positive seroconversion rate was calculated according to amounts of positive and negative samples under each dilution and then the antibody positive seroconversion rate was used to calculated ED$_{50}$ value (median effective dose) as follows.

$$ED_{50}\ value=10^{50\%\ terminal\ logarithm\ of\ seroconversion\ rate}$$

wherein 50% terminal logarithm of seroconversion rate=Logarithm of dilution degree (content) of above 50% seroconversion rate+distance ratio×dilution series logarithm Distance Ratio=(above 50% seroconversion rate−50%)/(above 50% seroconversion rate−below 50% seroconversion rate)

3.3 Results:

Table 4 provides effect of humoral immune response stimulated by the pharmaceutical composition of this example and the results of anti-HBs seroconversion rate induced by the pharmaceutical composition of this example, wherein the pharmaceutical composition comprising HBsAg and Al(OH)$_3$ as well as CpG-ODN with various concentrations thereof.

TABLE 4

| Number# | concentration (μg/ml) | | Seroconversion rate (%) | | | | | ED50 |
|---|---|---|---|---|---|---|---|---|
| | Al(OH)$_3$ | CpG | 1:16 | 1:32 | 1:64 | 1:128 | 1:256 | |
| 1# | 300 | 125 | 100 | 100 | 87.5 | 50 | — | 0.170 |
| 2# | | 250 | 100 | 100 | 100 | 37.5 | — | 0.179 |
| 3# | | 500 | 100 | 100 | 87.5 | 50 | — | 0.170 |
| 4# | 400 | 125 | — | 100 | 100 | 75 | 0 | 0.124 |
| 5# | | 250 | — | 100 | 100 | 50 | 0 | 0.156 |
| 6# | | 500 | — | 100 | 87.5 | 87.5 | 0 | 0.122 |
| 7# | 500 | 125 | — | 87.5 | 100 | 37.5 | 12.5 | 0.178 |
| 8# | | 250 | — | 100 | 87.5 | 37.5 | 0 | 0.191 |
| 9# | | 500 | — | 100 | 100 | 75 | 0 | 0.124 |
| 10# | 500 | 0 | — | 100 | 75 | 12.5 | 0 | 0.235 |

From the above table, it can be seen that ED$_{50}$ value of mouse immunized by 10# sample is 0.235, while ED$_{50}$ values of mice immunized by 1# to 9# samples are less than 0.2, therefore, ED$_{50}$ values of the mice immunized by 1# to 9# samples has significant difference over ED$_{50}$ value of mouse immunized by 10# (P<0.05). This indicates that seroconversion rates of the mice immunized by the vaccines formulated with both aluminium hydroxide and CpG-ODN as adjuvants are remarkably increased, which verifies that CpG-ODN and aluminium hydroxide have synergistic effect and both of them can be used in combination to improve the protective effect of vaccines.

Example 4: Specific Cell Immune Response Induced by Combination of Aluminium Hydroxide at Different Concentrations and CpG-ODN at Different Concentrations The following method was performed to detect the function of the pharmaceutical compositions on induction of specific cell immune response. The pharmaceutical compositions used in this example are the ones comprising HBsAg and Al(OH)$_3$ as well as CpG-ODN with various concentrations thereof provided in Example 3.

4.1 Materials and Reagents:

Animals for experimentation: clean degree BALB/C female mice, 4 to 6 weeks old (purchased from Vital River Laboratory Animal Technology Co. Ltd.), body weight: 15 to 25 g, 8 mice per group.

HBsAg stock (without aluminium adjuvant, purchased from National Vaccine & Serum Institute): prepared by dissolving 1 mg HBsAg protein lyophilized powder in 1 ml PBS for use.

CpG-ODN (5'-tcgacgttcgtcgttcgtcgttc-3', SEQ ID NO. 1, purchased from Beijing DNA Biotechnology Co., Ltd.) solution: prepared by dissolving various amount of CpG- ODN in sterile physiological saline solution, one day before use, standing at 4° C. overnight for use.

Al(OH)$_3$ solution: prepared by dissolving various amount of Al(OH)$_3$ in sterile physiological saline solution.

4.2 Method:

50 µl solution of mixture comprising CpG-ODN solution, aluminium hydroxide solution and HBsAg solution with various concentrations was placed on ice for 10 min and then diluted. 100 µl diluted sample (containing 1 µg hepatitis B surface antigen) was injected into left anterior tibialis of female BALB/C mice (4 to 5 weeks old, 8 mice per group). The mice were immunized at 0 week and 4 weeks and euthanized at 5 weeks. Spleen was collected to prepare spleen cells. PVDF membrane 96-well plate was coated by anti-IFN-γ antibody. Spleen lymphocytes were prepared and counted. The 96-well plate was blocked to incubate cells. Next, the plate was washed to develop. ELISPOT plate was placed in automatic reading board instrument for CTL Enzyme-linked immune spot analysis device to adjust parameters, collect images and proceed with counting.

Figure 5:
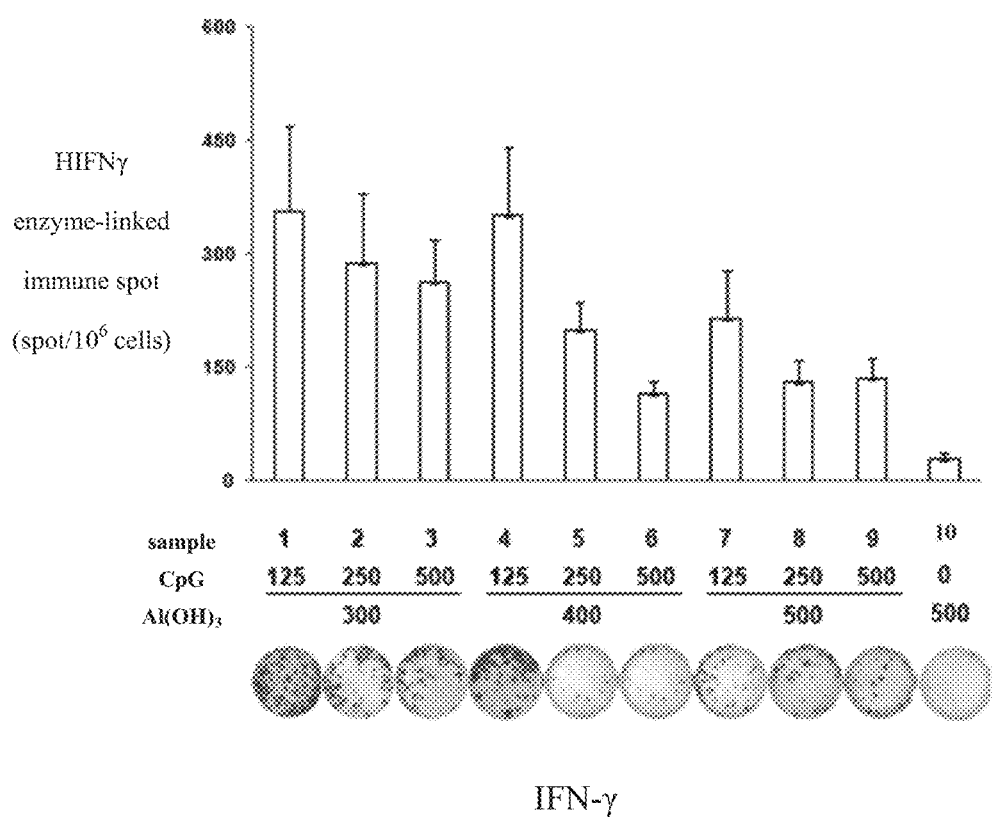
FIG. 5 shows variation on amount of IFN-γ, wherein CpG with different concentrations and aluminium adjuvant with different concentrations are used in combination to induce production of IFN-γ in mice.

4.3 Result:

As shown in FIG. 5, under the condition that aluminium hydroxide has a concentration of 300 µg/ml and CpG-ODN has a concentration of 125 µg/ml, the spots in the collected image are the most intensive, i.e., the combination quantity of antigens and antibodies is the greatest; next is the condition that aluminium hydroxide has a concentration of 400 µg/ml and CpG-ODN has a concentration of 125 µg/ml; followed by the condition that aluminium hydroxide has a concentration of 300 µg/ml and CpG-ODN has a concentration of 250 µg/ml. However, under the condition that no CpG-ODN was contained in the vaccine, few spots can be seen in the collected image, that is to say, antigens don't combine with antibodies. This reveals that 10# vaccine only comprising aluminium hydroxide induces IFN-γ expression at lower level than 1# to 9# vaccines comprising both aluminium hydroxide and CpG-ODN as double adjuvants. The vaccine only comprising aluminium hydroxide as adjuvant is able to stimulate Th2 immune response, but induction of Th1 cell immune response is not satisfying. 1# to 9# vaccines comprising both aluminium hydroxide and CpG-ODN as double adjuvants induce IFN-γ expression at remarkably higher level than 10# vaccine only comprising aluminium hydroxide. The research on humoral immune response also shows that vaccines comprising both aluminium hydroxide and CpG-ODN as double adjuvants produce higher level of antibodies than the vaccine only comprising aluminium hydroxide, which indicates that use of aluminium hydroxide and CpG-ODN in combination in Hepatitis B vaccines will exhibit synergistic effect that not only boost humoral immune but also induce IFN-γ expression and activate Th1 cell immune response. The vaccines with double adjuvants disclosed in the present invention have more advantageous over traditional vaccines that only comprises aluminium hydroxide as adjuvant. Therefore, the vaccines with double adjuvants disclosed in the present invention have therapeutical and prophylactic effect, thereby, having practical potential.

CONCLUSION

The pharmaceutical composition comprising (a) antigen with a concentration ranging from 1 µg/ml to 100 µg/ml, (b) CpG oligonucleotide having a sequence of 5'-tcgacgttcgtcgt-tcgtcgttc-3', with a concentration ranging from 25 µg/ml to 500 µg/ml, and (c) aluminium adjuvant with a concentration ranging from 25 µg/ml to 500 µg/ml, as disclosed in the present invention, is able to induce immune response against hepatitis B surface antigen and boost immune effect of Hepatitis B vaccines. The pharmaceutical composition with double adjuvants as disclosed in the present invention can be used as vaccine, which exhibits advantageous over traditional vaccine only comprising aluminium hydroxide. Double adjuvants in the vaccine exhibit synergistic effect that not only boost humoral immune, but also activate Th1 cell immune response. The vaccine prepared from the pharmaceutical composition of the present invention can not only neutralize virus outside cells but also completely clean virus hiding in the infected cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. The scope of the invention is indicated by the appended claims. All changes that come within the meaning of, and range of, equivalency of the claims are intended to be embraced therein.

The invention claimed is:

1. A pharmaceutical composition for inducing immune response to hepatitis C virus in a subject, comprising:
   (a) a hepatitis C virus-related antigen with a concentration ranging from 1 µg/ml to 100 µg/ml;
   (b) CpG oligonucleotides having a sequence of 5'-tcgacgt-tcgtcgttcgtcgttc-3' (SEQ ID NO: 1), with a concentration ranging from 25 µg/ml to 500 µg/ml, and
   (c) an aluminium adjuvant with a concentration ranging from 25 µg/ml to 500 µg/ml.

2. The pharmaceutical composition of claim 1, wherein, the sequence of the said CpG oligonucleotides is 5'-tcgacgt-tcgtcgttcgtcgttc-3' (SEQ ID NO: 1).

3. The pharmaceutical composition of claim 1, wherein, the aluminium adjuvant comprises aluminium hydroxide.

4. The pharmaceutical composition of claim 1, wherein, the aluminium adjuvant has a concentration ranging from 25 μg/ml to 125 μg/ml, or from 125 μg/ml to 500 μg/ml, or from 125 μg/ml to 400 μg/ml, or from 125 μg/ml to 300 μg/ml, or from 250 μg/ml to 500 μg/ml, or from 300 μg/ml to 400 μg/ml, or from 400 μg/ml to 500 μg/ml, or from 300 μg/ml to 500 μg/ml.

5. The pharmaceutical composition of claim 1, wherein, the CpG oligonucleotides with the sequence of 5'-tcgacgt-tcgtcgttcgtcgttc-3' (SEQ ID NO: 1) have a concentration ranging from 125 μg/ml to 500 μg/ml, or from 25 μg/ml to 125 μg/ml, or from 125 μg/ml to 250 μg/ml, or from 250 μg/ml to 500 μg/ml.

6. The pharmaceutical composition of claim 1, wherein, the antigen has a concentration of 20 μg/ml.

7. The pharmaceutical composition of claim 1, wherein, the antigen has a concentration of 20 μg/ml, the CpG oligonucleotides have a concentration of 500 μg/ml, the aluminium adjuvant has a concentration of 25 μg/ml; or the antigen has a concentration of 20 μg/ml, the aluminium adjuvant has a concentration of 25 μg/ml, the CpG oligonucleotides have a concentration of 125 μg/ml; or the antigen has a concentration of 20 μg/ml, the aluminium adjuvant has a concentration of 125 μg/ml, the CpG oligonucleotides have a concentration of 25 μg/ml; or the antigen has a concentration of 20 μg/ml, the aluminium adjuvant has a concentration of 300 μg/ml, the CpG oligonucleotides have a concentration of 125 μg/ml; or the antigen has a concentration of 20 μg/ml, the aluminium adjuvant has a concentration of 400 μg/ml, the CpG oligonucleotides have a concentration of 125 μg/ml; or the antigen has a concentration of 20 μg/ml, the aluminium adjuvant has a concentration of 125 μg/ml, the CpG oligonucleotides have a concentration of 500 μg/ml.

8. The pharmaceutical composition of claim 1, further comprising pharmaceutically acceptable excipients.

* * * * *

```
SEQUENCE LISTING

<160> NUMBER OF SEQ ID NOS: 1

<210> SEQ ID NO 1
<211> LENGTH: 23
<212> TYPE: DNA
<213> ORGANISM: Artificial Sequence
<220> FEATURE:
<223> OTHER INFORMATION: CpG Oligonucleotide

<400> SEQUENCE: 1
tcgacgttcg tcgttcgtcg ttc                                           23
```